United States Patent
Yamazaki

(10) Patent No.: US 10,512,319 B2
(45) Date of Patent: Dec. 24, 2019

(54) WARM-COOL BEAUTY TREATMENT DEVICE

(71) Applicant: YA-MAN LTD., Tokyo (JP)

(72) Inventor: Iwao Yamazaki, Tokyo (JP)

(73) Assignee: Ya-Man Ltd., Tokyo (JP)

( * ) Notice: Subject to any disclaimer, the term of this patent is extended or adjusted under 35 U.S.C. 154(b) by 393 days.

(21) Appl. No.: 14/597,556

(22) Filed: Jan. 15, 2015

(65) Prior Publication Data

US 2015/0121900 A1    May 7, 2015

Related U.S. Application Data

(63) Continuation of application No. PCT/JP2013/004584, filed on Jul. 29, 2013.

(30) Foreign Application Priority Data

Jul. 31, 2012  (JP) .................................. 2012-169459
Aug. 29, 2012  (JP) .................................. 2012-188307

(51) Int. Cl.
  *A45D 44/00*  (2006.01)
  *F25B 21/04*  (2006.01)
  *A61F 7/00*  (2006.01)

(52) U.S. Cl.
  CPC .............. *A45D 44/00* (2013.01); *F25B 21/04* (2013.01); *A45D 2200/155* (2013.01);
  (Continued)

(58) Field of Classification Search
  CPC ................ A61F 7/00; A61F 2007/0075; A61F 2007/0298; A61F 2007/0087;
  (Continued)

(56) References Cited

U.S. PATENT DOCUMENTS 3,207,159 A * 9/1965 Tateisi ................... A61B 18/02
                                                    607/96
4,640,284 A * 2/1987 Ruderian ................ A61F 7/007
                                                    126/204
(Continued)

FOREIGN PATENT DOCUMENTS

CN       2269567 Y    12/1997
CN       1303659 A     7/2001
(Continued)

OTHER PUBLICATIONS

English-language International Search Report issued by the Japanese Patent Office in International Application No. PCT/JP2013/004584, dated Aug. 20, 2013 (2 pages).
(Continued)

*Primary Examiner* — Frantz F Jules
*Assistant Examiner* — Martha Tadesse
(74) *Attorney, Agent, or Firm* — Finnegan, Henderson, Farabow, Garrett & Dunner, L.L.P.

(57) ABSTRACT

A warm-cool beauty treatment device, comprising: a Peltier element of a plate shape having a first surface configured to generate heat, and a second surface configured to absorb heat; a heat sink including—a first section touching the first surface, and a second section connecting the first section thermally; a first plate connected to the first surface thermally via the heat sink; a second plate connected to the second surface thermally; a blower configured to produce air flow to release the heat of the second section; and a power supply configured to supply electric power to the Peltier element and the blower.

16 Claims, 6 Drawing Sheets

Figure 1A:
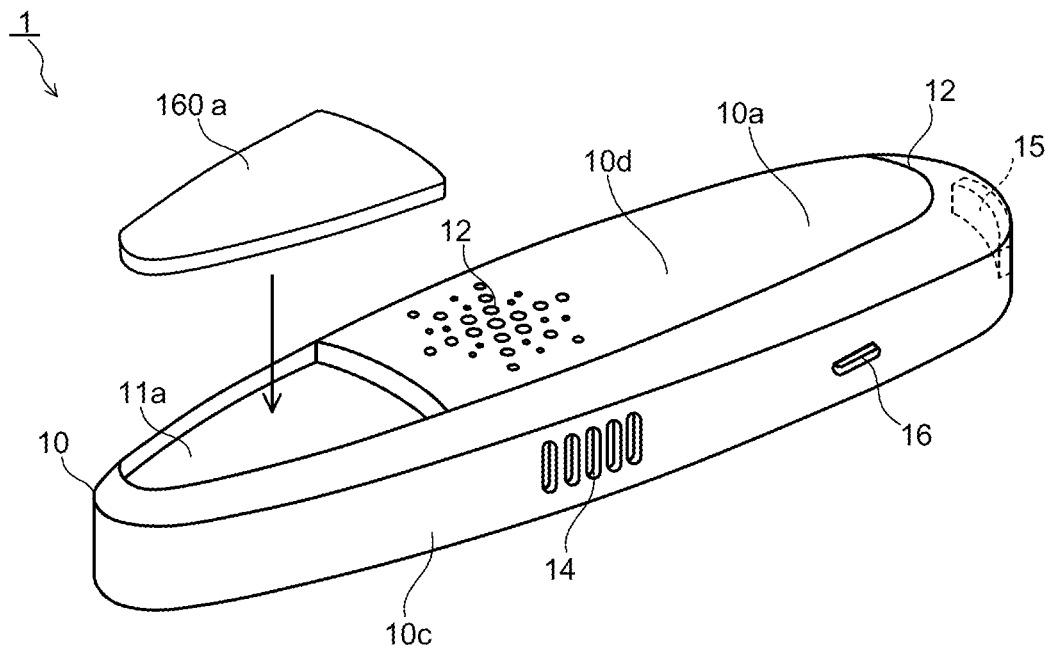

(52) U.S. Cl.
CPC ............... *A61F 2007/0075* (2013.01); *A61F 2007/0077* (2013.01); *F25B 2321/02* (2013.01)

(58) Field of Classification Search
CPC ...... A61F 2007/0086; A61F 2007/0078; A61F 2007/0077; A61F 2007/0052; H01L 23/38; G05D 23/24; F25B 2321/0212; F25B 2321/02; A45D 2200/155
See application file for complete search history.

(56) References Cited

U.S. PATENT DOCUMENTS

| | | | | |
|---|---|---|---|---|
| 4,915,108 | A * | 4/1990 | Sun | A61F 7/007 |
| | | | | 219/211 |
| 5,207,674 | A * | 5/1993 | Hamilton | A61B 18/02 |
| | | | | 606/20 |
| 5,209,227 | A * | 5/1993 | Deutsch | A61M 35/003 |
| | | | | 607/104 |
| 5,327,886 | A * | 7/1994 | Chiu | A61F 7/007 |
| | | | | 601/15 |
| 5,578,014 | A * | 11/1996 | Erez | A61F 7/10 |
| | | | | 604/192 |
| 5,628,769 | A * | 5/1997 | Saringer | A61F 7/007 |
| | | | | 607/98 |
| 5,634,472 | A * | 6/1997 | Raghuprasad | A61B 5/4824 |
| | | | | 600/555 |
| 5,800,490 | A * | 9/1998 | Patz | A61F 7/007 |
| | | | | 607/108 |
| 6,017,337 | A * | 1/2000 | Pira | A61B 18/02 |
| | | | | 601/15 |
| 6,567,696 | B2 * | 5/2003 | Voznesensky | A61F 7/007 |
| | | | | 607/108 |
| 6,648,907 | B2 * | 11/2003 | Larnard | A61F 7/12 |
| | | | | 607/105 |
| 6,679,908 | B2 * | 1/2004 | Shimizu | A61F 7/02 |
| | | | | 607/109 |
| 2001/0007952 | A1 | 7/2001 | Shimizu | |
| 2004/0171970 | A1 * | 9/2004 | Schleuniger | A61B 8/546 |
| | | | | 601/2 |
| 2005/0193742 | A1 * | 9/2005 | Arnold | A41D 13/005 |
| | | | | 62/3.5 |
| 2007/0193278 | A1 * | 8/2007 | Polacek | A61F 7/10 |
| | | | | 62/3.2 |
| 2010/0008036 | A1 | 1/2010 | Risher-Kelly | |
| 2011/0040235 | A1 | 2/2011 | Castel | |
| 2016/0242956 | A1 * | 8/2016 | Pilby Gomez | A61F 7/007 |

FOREIGN PATENT DOCUMENTS

| | | |
|---|---|---|
| CN | 2486144 Y | 4/2002 |
| CN | 101584097 A | 11/2009 |
| JP | 2000/037412 | 2/2000 |
| JP | 2001-190586 | 7/2001 |
| JP | 2000-210325 | 1/2005 |
| JP | 2005-006837 | 1/2005 |
| KR | 2001-0077967 | 8/2001 |

OTHER PUBLICATIONS

Written Opinion and Search Report from Intellectual Property Office of Singapore dated Feb. 4, 2016, in counterpart Singapore Patent Application No. 11201500685P.

International Preliminary Report on Patentability and Written Opinion issued by the International Bureau of WIPO dated Feb. 12, 2015, for International Patent Application No. PCT/JP2013/004584.

* cited by examiner

WARM-COOL BEAUTY TREATMENT DEVICE

CROSS-REFERENCE TO RELATED APPLICATIONS

This application is a continuation of prior International Application No. PCT/JP2013/004584 filed on Jul. 29, 2013, which is based upon and claims the benefit of priority from Japanese Patent Applications No. 2012-169459 filed on Jul. 31, 2012 and No. 2012-188307 filed on Aug. 29, 2012; the entire contents of all of which are incorporated herein by reference.

FIELD

The present invention relates to a beauty treatment device capable of giving a skin surface a warm sense/cool sense by using a thermoelectric element such as a Peltier element.

BACKGROUND

There is conventionally known a beauty treatment device which gives a skin surface a warm sense or a cool sense so that an effect of accelerating beautification or healing can be obtained, by using a Peltier element, in which a temperature difference appears on a front surface and a rear surface.
In obtaining a cool sense effect by such a beauty treatment device, there is a case where a member around a high-temperature surface of the Peltier element is heated and comes to have a high temperature and the cool sense effect of a low-temperature surface is diminished. Thus, it is necessary to actively release heat generated in the high-temperature surface.
A beauty treatment device having a heat releasing function on the high-temperature surface of the Peltier element as above is suggested. That beauty treatment device has a fin for heat releasing which is disposed near the high-temperature surface of the Peltier element and a blowing fan sending air to this fin. As a result that air is sent from the blowing fan toward the fin, heat generated in the high-temperature surface of the Peltier element is radiated.
Further, there is also suggested a warm-cool beauty equipment which is having heat storage medium to maintain a temperature of a high-temperature surface at the target temperature. The heat storage medium whose phase changes from a solid phase to a liquid phase at a target temperature, is disposed on a high-temperature surface side of a Peltier element.
However, in the beauty treatment device of Patent Document 1, it is difficult to have a broad contact surface between the heat release fin and the high-temperature surface of the Peltier element, and efficient release of heat in the high-temperature surface of the Peltier surface is difficult.
Further, in the warm-cool beauty equipment of Patent Document 2, there is a structural restriction on having a large heat capacity of the heat storage medium. Therefore, there is a problem that all the heat storage media become liquid after being used continuously for a long time and that a heat releasing characteristic is reduced.

DETAILED DESCRIPTION OF THE DRAWINGS

Figure 1B:
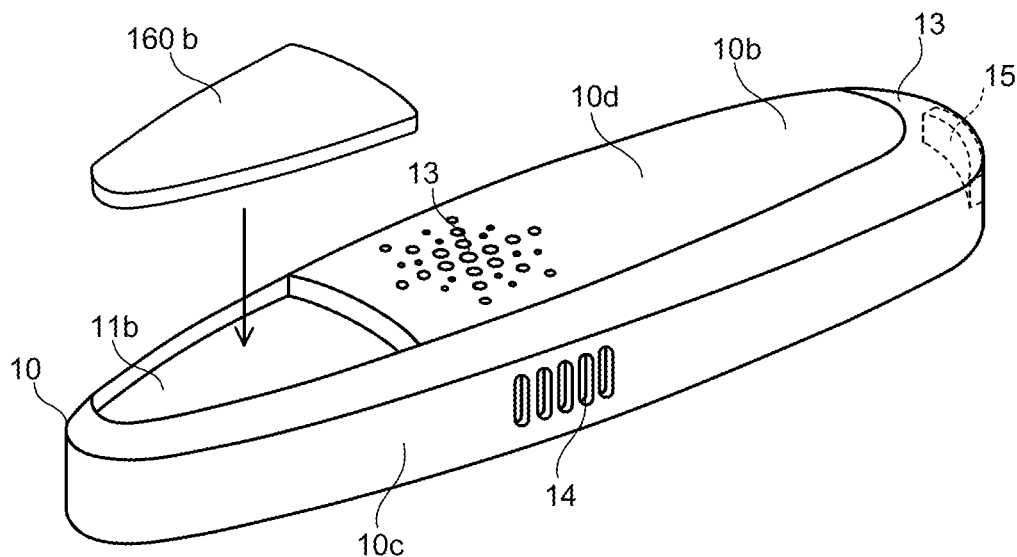
Figure 2:
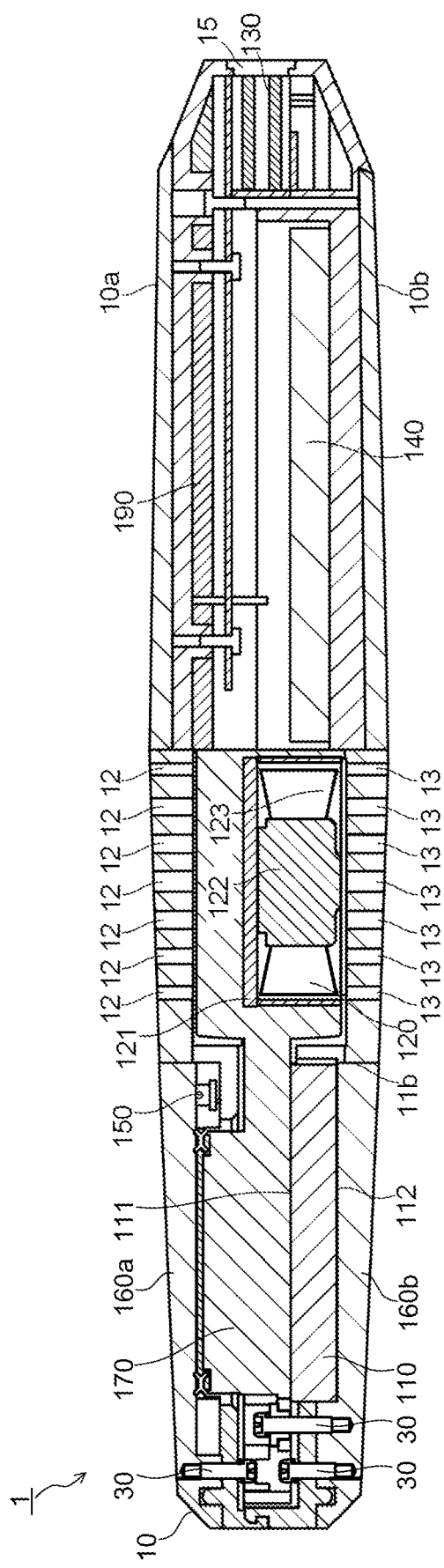
Figure 3A:
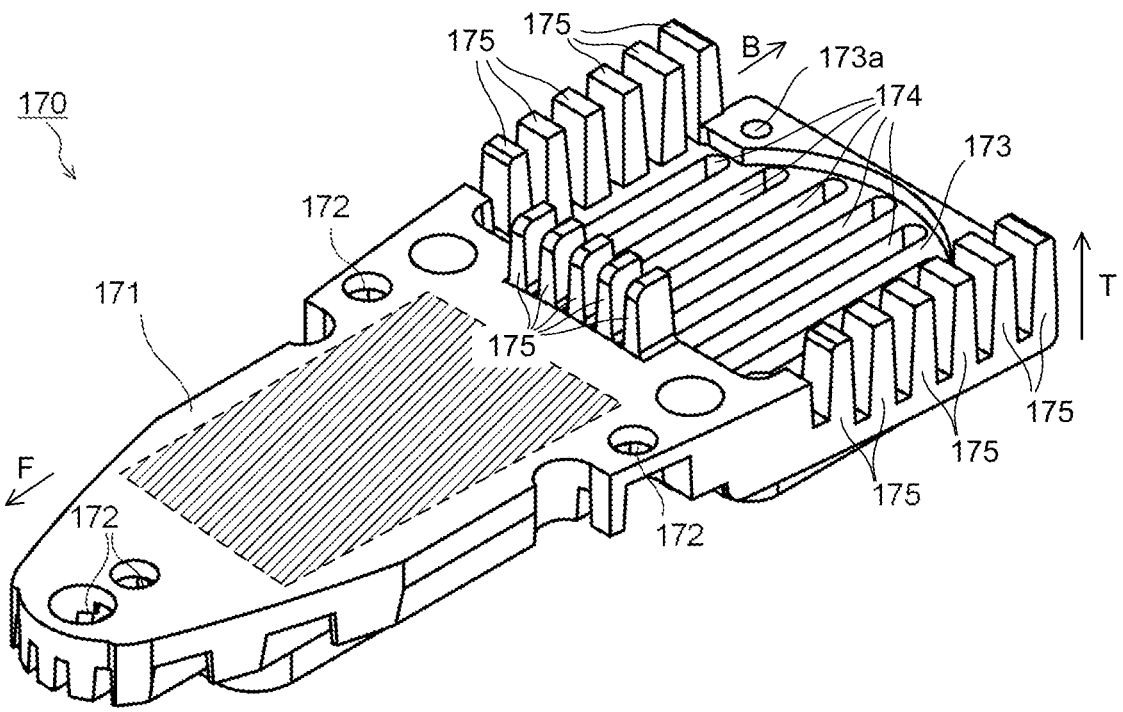
Figure 3B:
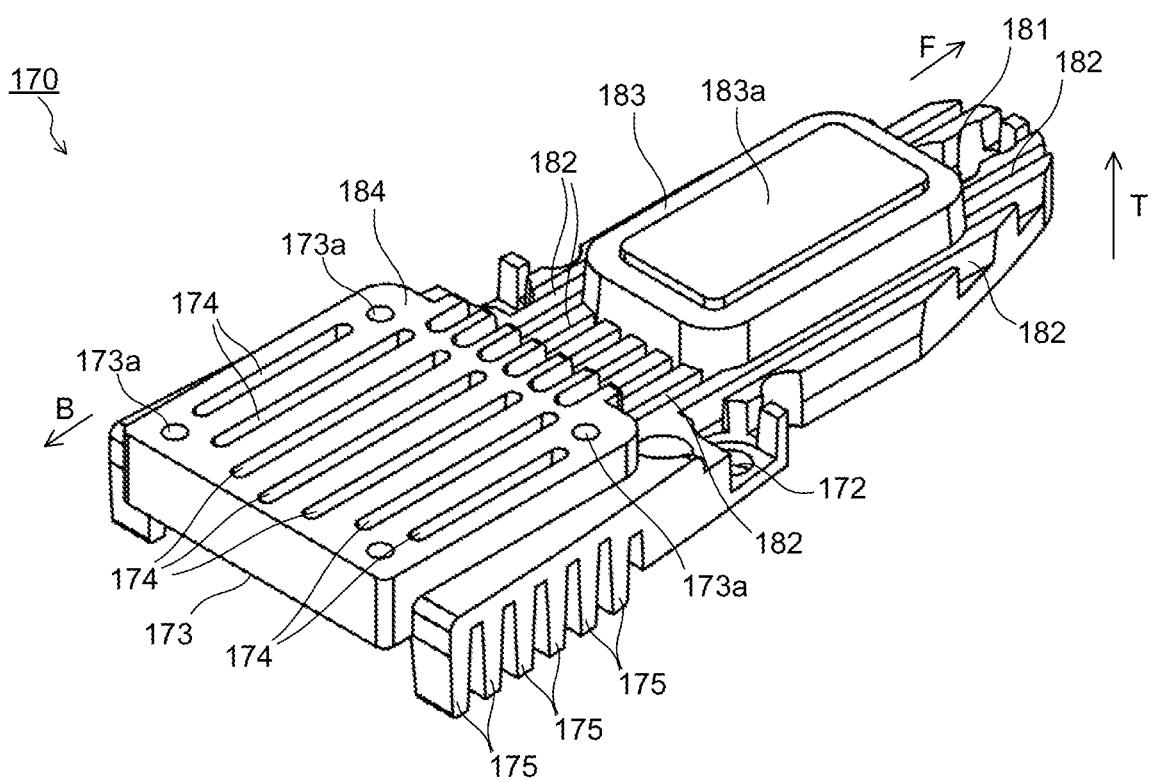
Figure 4:
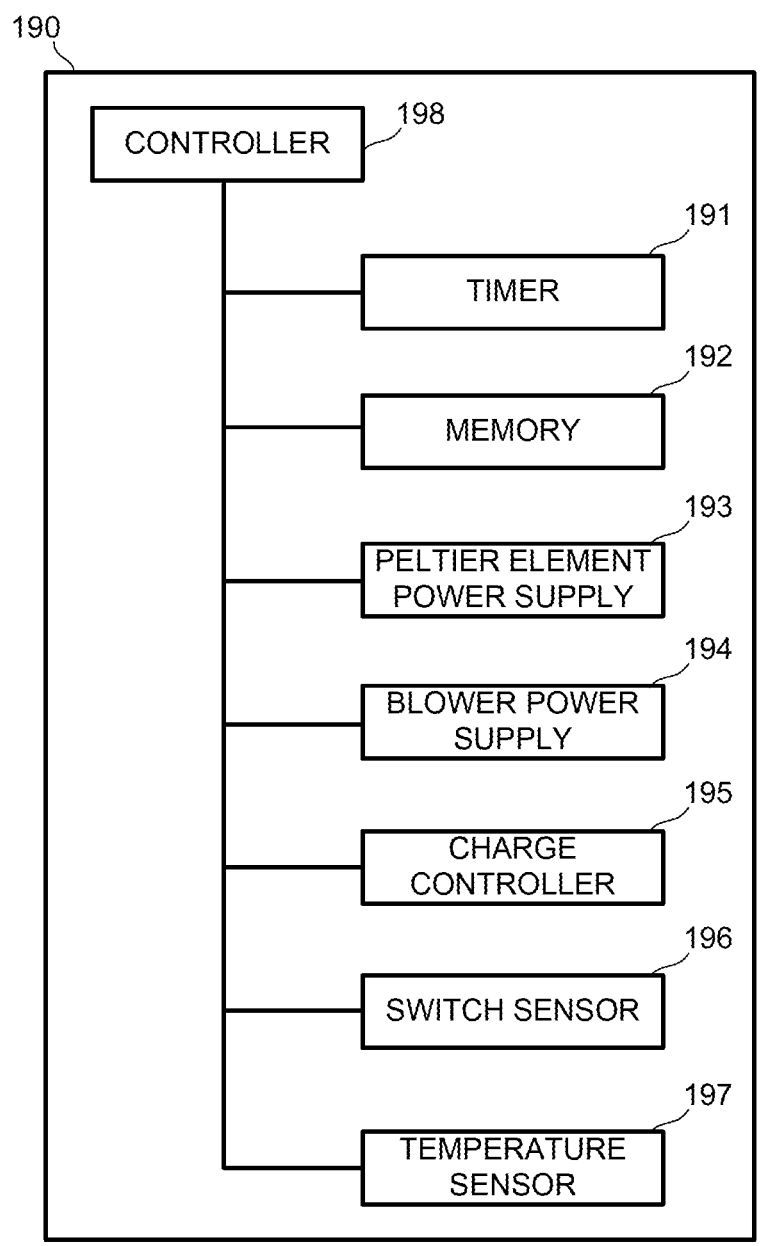
Figure 5:
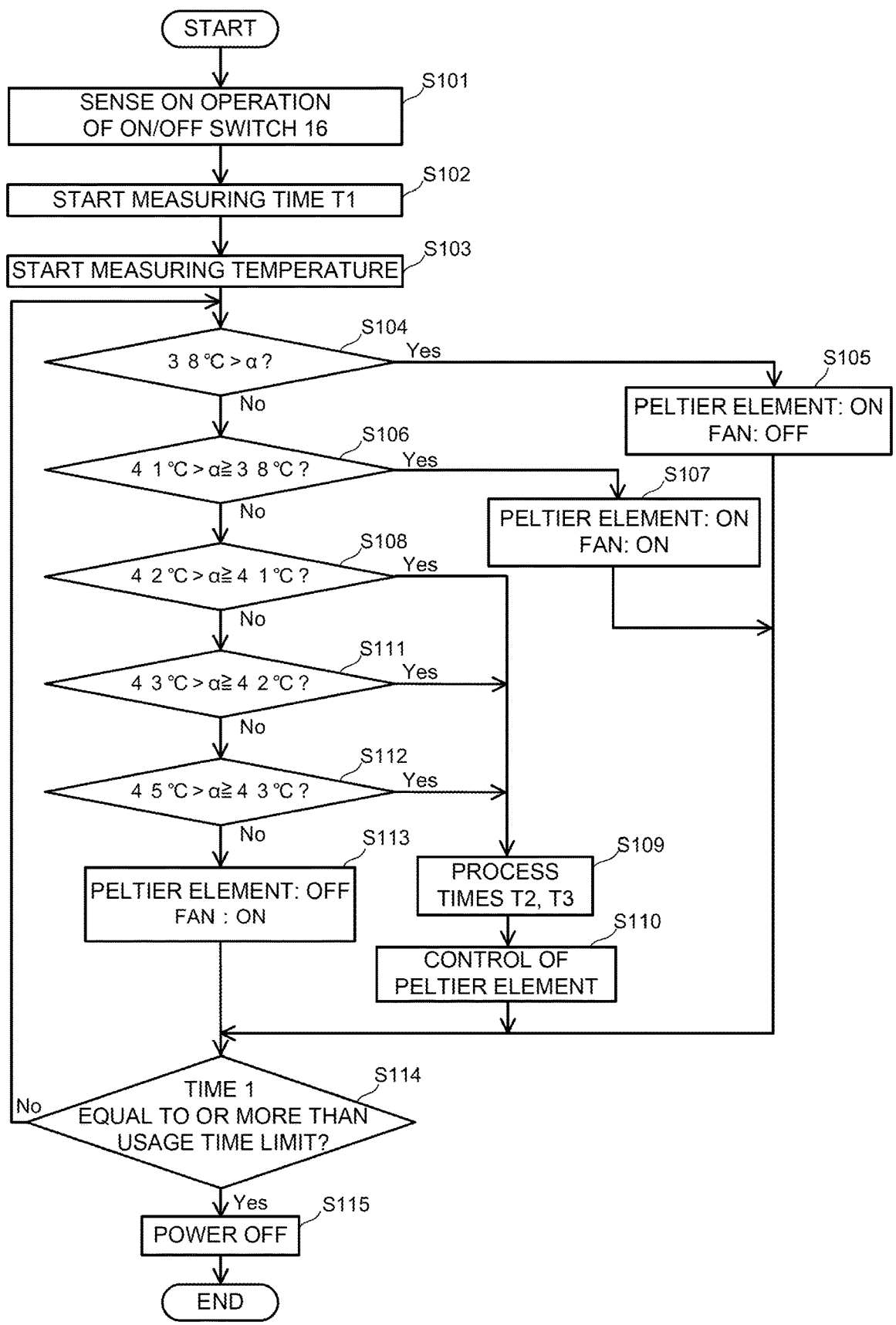
Figure 6:
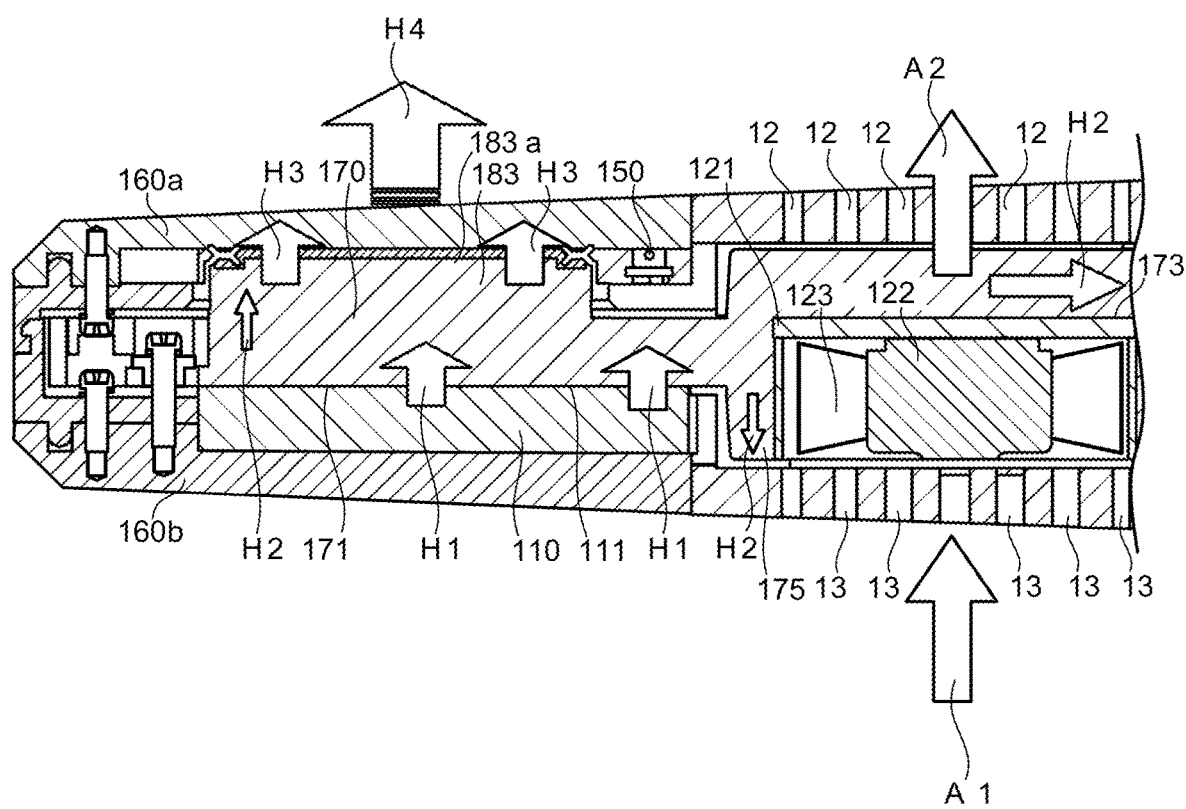

FIG. 1A is a perspective view of a warm-cool beauty treatment device 1; FIG. 1B is a perspective view of the warm-cool beauty treatment device 1 shown in FIG. 1A viewed from a rear side;
FIG. 2 is a partial cross-sectional view of the warm-cool beauty treatment device 1;
FIG. 3A is a perspective view of a heat sink 170; FIG. 3B is a perspective view of the heat sink 170 shown in FIG. 3A viewed from a rear side;
FIG. 4 is a functional block diagram of an electronic circuit substrate 190;
FIG. 5 is a flowchart showing an operation of the warm-cool beauty treatment device 1; and
FIG. 6 is a schematic diagram showing transfer of heat by the heat sink 170.

DETAILED DESCRIPTION

Embodiments are made to cope with the above-described circumstances and its object is to provide a warm-cool beauty treatment device capable of effectively releasing or using heat of a high-temperature surface of a Peltier element.
A warm-cool beauty treatment device of an embodiment of the present invention has: a casing provided with a first surface, a second surface on an opposite side of the first surface, and a plurality of openings; a Peltier element of a plate shape housed in the casing; a heat sink housed in the casing and having a planar heat absorbing section in which the Peltier element is arranged in a manner that a heat releasing surface of the Peltier element abuts thereon and a heat releasing section in which a penetrating hole is formed in a direction orthogonal to a surface on which the Peltier element is arranged and which is arranged in a position corresponding to the opening of the casing; a blowing unit disposed close to the heat releasing section in the casing; a cool-side plate arranged on a heat absorbing surface side of the Peltier element in a manner to be exposed from the first surface; a warm-side plate arranged on a surface of an opposite side of the surface which abuts on the Peltier element of the heat absorbing section in a manner to be exposed from the second surface; and a power supply means supplying electric power to the Peltier element and the blowing unit.
The warm-cool beauty treatment device of the embodiment of the present invention may further have: a temperature measurement means in contact with the cool-side plate or the warm-side plate and measuring a temperature of the cool-side plate or the warm-side plate; and a control section controlling supply of electric power to the Peltier element and/or the blowing unit in correspondence with the temperature measured by the temperature measurement unit.
The warm-cool beauty treatment device of the embodiment of the present invention can be configured to further have a timer clocking a time, wherein the control section controls a supply time of electric power to the Peltier element and/or the blowing unit in correspondence with the clocked time of the timer.
The power supply means may be a secondary battery storing electric power. The temperature measurement device may be a thermistor.
The warm-cool beauty treatment device of the embodiment of the present invention is desired to be configured that the cool-side plate and the warm-side plate come into usable states simultaneously by start of electric power supply from the power supply means, and that each plate is able to be in contact with a skin surface alternately without switching of a setting of the device.
According to the present invention, there can be provided a warm-cool beauty treatment device capable of effectively releasing or using heat of a high-temperature surface of a Peltier element.

Embodiment

Hereinafter, a warm-cool beauty treatment device 1 being an example of an embodiment of the present invention will be described with reference to the drawings. As shown in FIG. 2, in the warm-cool beauty treatment device 1 of this embodiment, a main part is constituted with a plate-shaped Peltier element 110, a cool plate 160b disposed on a heat absorbing surface 112 side of the Peltier element 110, a warm plate 160a disposed on a heat-generating surface 111 side via a heat sink 170, a blower 120, and a casing 10 housing the above.

As shown in FIG. 1A and FIG. 1B, the warm-cool beauty treatment device 1 has the warm plate 160a and the cool plate 160b in a front end part of the casing 10. Further, the casing 10 has a grip section 10d which is gripped for manipulation.

In the warm-cool beauty treatment device 1, supplying power to the Peltier element 110 brings about a state where the warm plate 160a and the cool plate 160b can be used simultaneously. Touching a skin surface of a person to receive treatment (user) with the plates, enable to stimulate the skin surface by warmness or coolness without changing a set-up of the warm-cool beauty treatment device 1, and to instantly switch the stimulation for the warm sense or the cool sense in use.

Here, an example of "changing a set-up of the device" is "changing a direction of an electric current flowing to the Peltier element 110". For example, there is sometimes suggested another beauty treatment device having a similar configuration to that of the warm-cool beauty treatment device 1. That beauty treatment device has one plate corresponding to the warm plate 160a or the cool plate 160b. In this beauty treatment device, it is configured that the one plate is in touch with one surface of another Peltier element corresponding to the Peltier element 110 the warm-cool beauty treatment device 1 has.

The beauty treatment device configured as above can have a switch, which is operated by a user, for switching forward and reverse of a direction of an electric current to flow to the Peltier element (in other words, switching a set-up of the device). By such a switch, one surface of one plate can be made to function as a warm plate or a cool plate.

However, in the above case, since the user is required to perform actuation of switch for switching the direction of the electric current, beauty treatment cannot be done easily. Further, there is a possibility that by providing such a switch a manufacturing cost of another beauty treatment device is increased from a case of manufacturing the warm-cool beauty treatment device 1 or that a yielding is deteriorated. The warm-cool beauty treatment device 1 is configured to be able to give the skin surface stimulation for the warm sense or the cool sense without "changing a set-up of the device" as above, and to be able to instantly switch (changeover) the stimulation for the warm sense or the cool sense. Thereby, it is possible to prevent the user from feeling that beauty treatment is complicated. Therefore, the user can easily perform beauty treatment. Further, for a similar reason, the manufacturing cost can be made lower compared with another beauty treatment device.

The casing 10 is a box body having a front surface 10a whose planar shape is almost tear-drop shaped, a rear surface 10b being a rear side of the front surface 10a, and a side surface 10c connecting the front surface 10a and the rear surface 10b. In front end parts of tapered shapes of the front surface 10a and the rear surface 10b, there are each provided a warm plate fitting hole 11a and a cool plate fitting hole 11b penetrating to the inside of the casing 10 for exposing surfaces of the warm plate 160a and the cool plate 160b.

In a neighborhood of an edge part of the warm plate fitting hole 11a on almost a center part side of the front surface 10a, numerous exhaust holes 12 being a part of a ventilating window penetrating to the inside of the casing 10 are provided. Similarly, in a neighborhood of an edge part of the cool plate fitting hole 11b on almost a center part of the rear surface 10b, numerous intake holes 13 being another part of the ventilating window penetrating to the inside of the casing 10 are provided.

In an almost center part of the side surface 10c, a plurality of slot-shaped exhaust holes 14 being a part of the ventilating window penetrating to the inside of the casing 10 is provided. The exhaust holes 14 are provided in predetermined two places of the side surface 10c in a manner to sandwich the exhaust hole 12 or the intake hole 13.

On an end side of the casing 10 of the side surface 10c, a power supply terminal exposing hole 15 is provided. A power code, which is not shown here, is inserted to the power supply terminal exposing hole 15 in a freely attachable/detachable manner.

In a predetermined place of the side surface 10c, an ON/OFF switch 16 for heating the warm plate 160a and for cooling the cool plate 160b is provided in a manner to expose a part thereof.

Next, an internal structure of the casing 10 will be described by using FIG. 2. As shown in FIG. 2, the casing 10 houses the Peltier element 110, the 120, a power supply terminal 130, a secondary battery 140, a thermostat 150, the warm plate 160a and the cool plate 160b, the heat skink 170, and an electronic circuit substrate 190. The casing 10 sometimes houses an AC-DC converter converting an alternating current into a direct current.

The Peltier element 110 is a thermoelectric element using a Peltier effect, in which heat transfer occurs as a result that an electric current flows in a joint surface of a joined metal or semiconductor different from each other. It is assumed that, in the Peltier element 110, a temperature difference between the heat generating surface 111 and the heat absorbing surface 112 when an electric current flows is about 30 degrees. The Peltier element 110 is disposed near the cool plate fitting hole 11b. The Peltier element 110 has the heat generating surface 111 connected to the warm plate 160a via the heat sink 170 and the heat absorbing surface 112 directly in contact with the cool plate 160b.

It is desirable that the Peltier element 110 is housed in the casing 10 in a manner that surroundings of the heat absorbing surface 112 in particular are enclosed by a heat insulator. Thereby, heat of the heat generating surface 111 can be prevented from going round to the heat absorbing surface 112 to cause temperature rise of the heat absorbing surface 112.

The blower 120 is a blower having a motor 122 and a fan 123 whose rotation shaft is a shaft of this motor 122 in a housing 121.

The blower 120 is fixed to a wall surface inside the casing 10 near the intake hole 13 by a screw, an adhesive, or the like. As a result that the blower 120 is provided near the intake hole 13, outside air to be blown to the heat sink 170 is sucked from the intake hole 13 into the inside of the casing 10 by rotation of the fan 123.

The power supply terminal 130 is provided inside the power supply terminal exposing hole 15. The power supply terminal 130 is an electric contact part for obtaining electric power to be supplied to the Peltier element 110, the blower 120, or the like from an outlet for home use or a personal computer.

The secondary battery 140 is a power supply for supplying electric power to the Peltier element 110 or the blower 120 when supply of electric power from the power supply terminal 130 is difficult. The secondary battery 140 is charged by electric power obtained from a commercial power supply. As the secondary battery 140, a battery of a lithium ion type, a nickel hydrogen type, or the like can be adopted, for example.

The thermostat 150 is electrically connected to the electronic circuit substrate 190 and functions as a temperature measurement means. The thermostat 150 is used to measure a temperature of the warm plate 160*a*. The thermostat 150 can be configured to have a thermistor, for example. It is possible to obtain information to correspond to the temperature of the warm plate 160*a* from a resistance value of the thermistor which changes in correspondence with temperature change of the warm plate 160*a*.

The warm plate 160*a* is a second contact plate. The cool plate 160*b* is a first contact plate. The warm plate 160*a* and the cool plate 160*b* are made of metal (for example, aluminum or copper) having a good thermal conductivity, formed into a plate shape. The warm plate 160*a* and the cool plate 160*b* are attached to the warm plate fitting hole 11*a* and the cool plate fitting hole 11*b* of the casing 10 with screws 30, respectively, in a manner to expose surfaces to touch a skin surface of a person to receive treatment to the outside.

Heat of the heat generating surface 111 of the Peltier element 110 is transferred to the warm plate 160*a* via the heat sink 170. Consequently, the warm plate 160*a* comes to be hotter than outside air.

The temperature of the warm plate 160*a* is adjusted at a predetermined temperature as a result that heat staying in the heat sink 170 is released by driving of the blower 120 or a time of ON/OFF of driving of the Peltier element 110 is controlled. In this embodiment, when beauty treatment is applied to the person to receive treatment, the temperature of the warm plate 160*a* is adjusted in a temperature range of 38° C. to 45° C. The cool plate 160*b* is deprived of heat by the heat absorbing surface 112 of the Peltier element 110. Consequently, the cool plate 160*b* comes to be cooler than outside air. In this embodiment, a temperature difference between the warm plate 160*a* and the cool plate 160*b* is about 25 to 30° C., and when beauty treatment is applied to the person to receive treatment, the temperature of the cool plate 160*b* is adjusted to be in a temperature range of 8° C. to 20° C. in correspondence with the temperature of the warm plate 160*a* having been adjusted.

Next, the heat sink 170 will be described in detail by using FIG. 3A and FIG. 3B.

The heat sink 170 is formed of metal (for example, aluminum or copper) having a good thermal conductivity. The heat sink 170 is formed to be oblong-shaped, and extends in a direction of the blower 120, going beyond a region where the Peltier element 110 is disposed, and is disposed in the casing 10. The heat sink 170 has a thickness sufficiently larger compared with the warm plate 160*a*, the cool plate 160*b*, and the Peltier element 110, and has a larger heat capacity compared with the warm plate 160*a* or the like.

As shown in FIG. 3A, the heat sink 170 has a flat surface 171 formed to be flat-shaped from a front end side (F side of FIG. 3A) to a center part. The heat sink 170 has a blower connection surface 173 in a rear end side (B side of FIG. 3A). The heat sink 170 has a plurality of heat release fins 175.

The flat surface 171 is provided with a plurality of screw holes 172 for fixing the heat sink 170 to the casing 10. The heat generating surface 111 of the Peltier element 110 is in close contact with a part (see a hatched region virtually shown in FIG. 3A) of the flat surface 171 via a heat-conductive grease or the like.

The housing 121 of the blower 120 is in contact with the blower connection surface 173. The blower connection surface 173 is provided with a screw hole 173*a* penetrating the heat sink 170 in a thickness direction (direction of an arrow T in FIG. 3A) for being fixed to the casing 10.

The blower connection surface 173 is provided with a plurality of slots 174 being slot-shaped holes penetrating the heat sink 170 in the thickness direction. Air sent by the blower 120 blows between the plural slots 174.

The plural heat release fins 175 are protrusions whose cross-sections are almost trapezoidal. The plural heat release fins 175 are protrudingly provided along the thickness direction (direction of the arrow T) of the heat sink 170. The plural heat release fins 175 are provided in a side edge part of the heat sink 170 and in a boundary part between the flat surface 171 and the blower connection surface 173, and are provided to surround the blower connection surface 173 as a whole. The heat release fin 175 provided in the side edge part of the heat sink 170 is intervened between a side surface of the blower 120 and the exhaust hole 14 of the casing 10. Consequently, air sent by the blower 120, while blowing between the respective heat release fins 175 provided in the side edge part of the heat sink 170, is discharged from the exhaust hole 14.

As shown in FIG. 3B, the heat sink 170 has a groove forming surface 181 being a surface of an opposite side of the flat surface 171. The groove forming surface 181 is provided with a plurality of grooves 182 along a longitudinal direction (direction from the front end side F to a rear end side B) of the heat sink 170. By the groove 182, a surface area in contact with air of the heat sink 170 is increased, and a heat releasing performance of the heat sink 170 is improved.

A warm plate contact mount 183 is formed in a center part of the groove forming surface 181. A front end surface 183*a* of the warm plate contact mount 183 is provided to be in close contact with the warm plate 160*a* via a heat-conductive grease or the like.

The heat sink 170 has an exhaust surface 184 being a surface which is an opposite side of the blower contact surface 173 and which faces the exhaust hole 12. The exhaust surface 184 is formed to be flat-shaped.

As shown in FIG. 4, the electronic circuit substrate 190 has a timer 191, a memory 192, a Peltier element power supply 193, a blower power supply 194, a charge controller 195, a switch sensor 196, a temperature sensor 197, and a controller 198. An electric circuit is formed by various electronic elements such as an IC chip, a capacitor, and a coil, in the electronic circuit substrate 190. This electric circuit functions as the timer 191, the memory 192 . . . the controller 198.

The timer 191 is a timer which is controlled by the controller 198 to clock a time. It is possible that a plurality of the timers 191 are provided in the electronic circuit substrate as necessary to clock times at different timings respectively. The timer 191 transmits information indicating the clocked time to the controller 198.

The memory 192 can keep various tables in advance. For example, in a case where the thermistor is used for the thermostat 150, the memory 192 sometimes holds a table in which a resistance value of the thermistor and a value indicating a temperature of the warm plate 160a are associated with each other.

The memory 192 can holds, for example, a table in which a value indicating the temperature of the warm plate 160a measured by the thermostat 150 and numeric information indicating an ON/OFF time of electric power supply to the Peltier element 110, and numeric information indicating an ON/OFF time of electric power supply to the blower 120 are associated with one another.

The memory 192 can holds a voltage value of a voltage applied to the Peltier element 110 or the blower 120.

The memory 192 can hold time information indicating a usage time limit for using the warm-cool beauty treatment device 1 safely in advance.

The Peltier element power supply 193 is controlled by the controller 198 to carry out turning on/off of electric power supply to the Peltier element 110. Thereby, driving of the Peltier element 110 is turned on/off.

The blower power supply 194 is controlled by the controller 198 to turns on/off electric power supply to the blower 120. Thereby, driving of the blower 120 is turned on/off. The charge controller 195 is controlled by the controller 198 to turn on/off electric power supply to the secondary battery 140. Thereby, charging of the secondary battery 140 is turned on/off.

The switch sensor 196 senses a pressing operation of the ON/OFF switch 16 by a person to perform treatment. The switch sensor 196 notifies the controller 198 of the pressing operation of the ON/OFF switch 16.

The temperature sensor 197 is electrically connected to the thermostat 150 and measures the temperature of the warm plate 160a in collaboration with the thermostat 150. In a case where the thermostat 150 is the thermistor, as a result that the temperature sensor 197 reads a resistance value of the thermistor, the resistance value changing in correspondence with the temperature of the warm plate 160a, the temperature sensor 197 can consequently detect the temperature of the warm plate 160a. The temperature sensor 197 notifies the controller 198 of information indicating the measured temperature of the warm plate 160a. The controller 198 controls the timer 191, the memory 192, the Peltier element power supply 193, the blower power supply 194, the charge controller 195, the switch sensor 196, and the temperature sensor 197, respectively.

Concrete examples of control of the controller 198 will be shown in (1) to (6) below.

(1) The controller 198 constantly monitors a voltage of the secondary battery 140. Based on this voltage, the controller 198 controls the charge controller 195 to charge the secondary battery 140.

(2) The controller 198 carries out reading/writing of information from/to the memory 192.

(3) The controller 198, responding to reception of notice of a signal indicating a pressing operation of the ON/OFF switch 16 from the switch sensor 196, controls the Peltier element power supply 193 to drive the Peltier element 110.

(4) The controller 198 controls the Peltier element power supply 193 and/or the blower power supply 194 based on information indicating the temperature of the warm plate 160a from the temperature sensor 197, with reference to the table held by the memory 192, and turns on/off driving of the Peltier element 110 and/or the blower 120 for a predetermined time.

(5) The controller 198 instructs the timer 191 to start and to end clocking.

The controller 198 receives information of a time clocked by the timer 191, from the timer 191. The controller 198 can know how long (how many second, how many minutes, . . . ) the timer has clocked, from the information of the clocked time transmitted from the timer 191. The controller 198 can instruct the timer 191 to reset the clocked time at a predetermined timing (for example, simultaneously with an instruction to the timer 191 to stop clocking). By such a "reset instruction", the time clocked by the timer 191 returns to 0 (zero) and clocking can be started from 0 (zero) at a starting time of next clocking.

(6) Other than the above, in a case where an LED or a vibrator vibrating the warm plate 160a and the cool plate 160b, for example, is provided in the casing 10, the controller 198 controls turning on/off of driving thereof.

(Explanation of Operation)

Next, by using FIG. 5, an operation of the warm-cool beauty treatment device 1 will be described.

(1) Start of Operation and Forced Termination (Steps S101 to S103 and Steps S114, S115)

The switch sensor 196 senses an ON operation of the ON/OFF switch 16 by a person to perform treatment (step S101). On this occasion, the switch sensor 196 notifies the controller 198 that the ON operation of the ON/OFF switch 16 is sensed.

The controller 198, on receiving notice of detection of the ON operation of the ON/OFF switch from the switch sensor 196, makes the timer 191 clock a time T1 (step S102).

The time T1 is a time which is compared with a usage time limit of the warm-cool beauty treatment device 1 in order for safe use of the warm-cool beauty treatment device 1. The usage time limit is twelve minutes, for example. When the time T1 clocked by the timer 191 becomes equal to or more than the usage time limit, the controller 198 forcibly shuts off electric power supply to the Peltier element 110 and the blower 120, to terminate the operation of the entire warm-cool beauty treatment device 1 (steps S114, S115). On this occasion, the controller 198 resets clocking of the timer 191. When the timer 191 starts clocking of the time T1, the controller 198 controls the temperature sensor 197 to start measurement of a temperature $\alpha$ of the warm plate 160a in collaboration with the thermostat 150 (step S103).

(2) Driving 1 of the Peltier Element 110 and/or the Blower 120 (Steps S104, S105, Step S114)

The controller 198 controls turning on/off of electric power supply to the Peltier element 110 and/or the blower 120 in correspondence with the temperature $\alpha$ of the warm plate 160a notice of which is given by the temperature sensor 197. For example, when the temperature $\alpha$ of the warm plate 160a is lower than 38° C., the controller 198 controls the Peltier element power supply 193 to supply electric power to the Peltier element 110.

On this occasion, the controller 198 does not perform supply of electric power to the blower 120 (Yes in the step S104, the step S105). Consequently, a temperature of the heat generating surface 111 of the Peltier element 110 rises, and simultaneously, a temperature of the heat absorbing surface 112 comes down, and corresponding thereto, the temperature of the warm plate 160a rises and simultaneously the temperature of the cool plate 160b comes down.

Next, the controller 198 receives information indicating the time T1 from the timer 129, and judges whether or not the time T1 is equal to or more than a predetermined time (step S114).

If the time T1 clocked by the timer 191 is equal to or more than the usage time limit, the controller 198 executes a content of the step S115.

If the time T1 clocked by the timer 191 is shorter than the usage time limit (No in the step S114), the controller repeats processings after the step S104.

(3) Driving 2 of the Peltier Element 110 and/or the Blower 120 (Steps S106, S107, Step S114)

When the temperature α of the warm plate 160a notice of which is given by the temperature sensor 197 is 38° C. or more and 41° C. or less (Yes in a step S106), the controller 198 controls the blower power supply 194 to drive the blower 120 (step S107). By driving of the blower 120, the temperature of the heat generating surface 111 of the Peltier element 110, rises more slowly than in the step S105. The temperature of the heat absorbing surface 112 comes down slowly. In correspondence therewith, the temperature of the warm plate 160a also rises more slowly than in the step S105, and the temperature of the cool plate 160b comes down slowly.

(4) Driving 3 of the Peltier Element 110 and/or the Blower 120 (Steps S108 to S113, Step S114)

When the temperature α of the warm plate 160a notice of which is given by the temperature sensor 197 is in a range of 41° C. or more and 42° C. or less (Yes in a step S108), the controller 198 makes the timer 191 clock a time T2 or a time T3 (step S109). The time T2 is a time of turning on of electric power supply to the Peltier element. The time T3 is a time of turning off of electric power supply to the Peltier element 110. The controller 198 repeats processings of the steps S104 to S114 also while the timer 191 clocks the time T2 or the time T3. The controller 198 turns on or off supply of electric power to the Peltier element 110 for a time corresponding to the time T2 or the time T3 clocked by the timer 191 (step S110).

Concrete explanation will be done below. When the temperature α of the warm plate 160a notice of which is given by the temperature sensor 197 is in a range of 41° C. or more and 42° C. or less (Yes in the step S108), the controller 198 makes clocking of 45 msec (millisecond) be performed as the time T2. The controller 198 turns on driving of the Peltier element 110 until the timer 191 finishes clocking of 45 msec as the time T2. When the timer 191 finishes clocking of 45 msec as the time T2, the controller 198 resets clocking of the time T2 and subsequently makes clocking of 5 msec be performed as the time T3. The controller 198 turns off driving of the Peltier element 119 until the timer 191 finishes clocking of 5 ms as the time T3. The time T2 in a case where the temperature α of the warm plate 160a notice of which is given by the temperature sensor 197 is in a range of 42° C. or more and 43° C. or less (Yes in a step S111) is 40 msec, and the time T3 is 10 msec. The time T2 in a case where the temperature α of the warm plate 160a notice of which is given by the temperature sensor 197 is in a range of 43° C. or more and less than 45° C. (Yes in a step S112) is 35 msec, and the time T3 is 15 msec. As described above, the controller 198 controls electric power supply to the Peltier element 110 so that an ON time of driving of the Peltier element 110 becomes shorter and, in contrast, an OFF time of driving of the Peltier element 110 becomes longer, as the temperature α of the warm plate 160a approaches 45° C.

As a result that turning on/off of electric power supply to the Peltier element 10 is repeated every predetermined time, temperature rising of the heat generating surface 111 of the Peltier element 110 becomes further slower. Therefore, it is possible to prevent rapid temperature rising (what is called an overshoot) of the heat generating surface 111 of the Peltier element 110, and in correspondence therewith, it is possible to prevent rapid rising of the temperature of the warm plate 160a. By preventing rapid rising of the temperature of the Peltier element 110, the Peltier element 110 can be prevented from being broken by heat.

(5) Turning Off of the Peltier Element 110 and/or the Blower 120 (Step S113)

When the temperature α of the warm plate 160a notice of which is given by the temperature sensor 197 becomes 45° C. or more (No in the step S112), the controller 198 controls the Peltier element power supply 193 to turn off electric power supply to the Peltier element 110. On this occasion, since electric power supply to the blower 120 is still in an ON state, the temperature of the heat generating surface 111 of the Peltier element 110 gradually lowers.

The controller 198 repeats the above operation of (2) to (6) until the time T1 clocked by the timer 191 becomes equal to or more than the usage time limit (Yes in the step S114) or the switch sensor 196 senses an OFF operation of the ON/OFF switch by the person to perform treatment.

As a result that the controller 198 controls each section as described above, it becomes possible to stabilize the temperature α of the warm plate 160a in a range of 38 to 45° C. Consequently, it is possible to prevent the person to receive treatment from having a burn. Note that when the temperature α of the warm plate 160a is stabilized in the range of 38 to 45° C., a temperature of the cool plate 160b is stabilized in a range of 8° C. to 20° C.

As a result that the person to perform treatment makes the warm plate 160a or the cool plate 160b touch a skin surface in a state describe above, skin can be cooled or heated.

An effect of increasing metabolism of the skin can be expected by giving such a cool sense or a warm sense to the skin surface.

According to the warm-cool beauty treatment device 1, since surfaces of the warm plate 160a and of the cool plate 160b are exposed on the front surface 10a and the rear surface 10b of the casing 10, it is possible to simultaneously realize a state where the warm sense by the warm plate 160a is able to be supplied to the skin surface of the person to receive treatment and a state where the cool sense by the cool plate 160b is able to be supplied to the skin surface of the person to receive treatment. Thereby, a user can instantly select which for the warm sense and the cool sense is to be given to the skin surface, and it becomes possible to give a skin surface a large temperature difference in a short time, so that stimulation to the skin surface can be made large in a short time.

Further, according to the warm-cool beauty treatment device 1 of this example, as shown in FIG. 6, since a part of the flat surface 171 of the heat sink 170 is in surface contact with the heat generating surface 111 of the Peltier element 110, heat H1 of the heat generating surface 111 is transferred to a warm plate contact mount 183 side and a blower connection surface 173 side of the heat sink 170 efficiently. Consequently, the heat having been transferred from the heat generating surface 111 extends over the heat sink 170 evenly (see "H2" of FIG. 6), and the heat H1 can be stored in the entire heat sink 170. Part of the heat H1 stored in the heat sink 170 is transferred to the warm plate 160a via the front end surface 183a of the warm plate contact mount 183 (see "H3" in FIG. 6). Consequently, the warm plate 160a is heated and the heat H3 of the warm plate 160a is supplied to the skin surface of the person to receive treatment (see "H4" in FIG. 6).

Further, the other part of the heat H1 stored in the heat sink 170 is discharged to the outside of the casing 10 efficiently by wind (see "A1, A2" in FIG. 6) blowing between the plural slots 174 and heat release fins 175 (see FIG. 3A) by driving of the blower 120. Consequently, it becomes possible to release the heat of the heat generating surface 111 of the Peltier element 110 effectively.

Conventionally, in a Peltier element 110, heat of the heat generating surface 111 sometimes goes round to the heat absorbing surface 112, bringing about temperature rising of the heat absorbing surface 112. According to the warm-cool beauty treatment device 1 of this embodiment, as a result that the heat generating surface 111 of the Peltier element 110 and the flat surface of the heat sink 170 are brought into surface contact with each other, the heat of the heat generating surface 111 of the Peltier element 110 can be transferred to the heat sink 170 efficiently. Besides, by transferring this heat to the warm plate 160a and releasing this heat by driving of the blower 120, the heat of the heat generating surface 111 can be prevented from going round to the heat absorbing surface 112. Thereby, it becomes possible to make the temperature of the heat absorbing surface 112 easy to be lowered.

According to the warm-cool beauty treatment device 1, since the heat of the heat generating surface 111 of the Peltier element 110 is used to heat the warm plate 160a, an element such as a heater for heating the warm plate 160a is unnecessary. Consequently, it becomes easier to realize a lower cost in manufacturing of the warm-cool beauty treatment device 1. Further, since the element such as a heater is not necessary, space saving and energy saving of the warm-cool beauty treatment device 1 can be realized in the warm-cool beauty treatment device, and it becomes possible to miniaturize the warm-cool beauty treatment device 1.

According to the warm-cool beauty treatment device 1, as a result that the heat sink 170 is intervened between the Peltier element 110 and the warm plate 160a and that a part of the heat sink 170, going beyond the Peltier element 110, extends in a direction of the blower 120 and is connected to the blower 120, the entire warm-cool beauty treatment device 1 can be formed compactly.

Modification Example

The present invention can be further modified variously. For example, an electronic circuit substrate 190 may have a variable resistor so that a voltage applied to a Peltier element 110 or a blower 120 can be varied. In this case, a temperature of a heat generating surface 111 of the Peltier element 110 can be adjusted by such alteration of the voltage.

Further, in the above-described embodiment, the temperature of the warm plate 160a is measured by the thermostat 150, but a temperature of a cool plate 160b or a Peltier element 110 may be measured.

Further, it is possible that a secondary battery 140 is not had and that electric power is directly obtained from an outlet for home use, for example.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A warm-cool beauty treatment device, comprising:
   a Peltier element of a plate shape having a first surface configured to generate heat, and a second surface configured to absorb heat;
   a heat sink including a first section touching the first surface, and a second section in thermal connection with the first section;
   a first plate connected to the first surface thermally via the heat sink;
   a second plate connected to the second surface thermally;
   a blower configured to produce air flow to release the heat of the second section; and
   a power supply configured to supply electric power to at least one of the Peltier element or the blower;
   a temperature sensor configured to measure a temperature of at least one of the first plate or the second plate; and
   a controller programmed to control the supply of electric power to the Peltier element and the blower according to the temperature measured by the temperature sensor so that:
   the electric power is supplied to the Peltier element and is not supplied to the blower in response to the temperature measured by the temperature sensor being lower than a first temperature,
   the electric power is supplied to the Peltier element and the blower in response to the temperature measured by the temperature sensor being higher than the first temperature and lower than a second temperature, the second temperature being higher than the first temperature, and
   the electric power is not supplied to the Peltier element and is supplied to the blower in response to the temperature measured by the temperature sensor being higher than a third temperature, the third temperature being higher than the second temperature.

2. The warm-cool beauty treatment device according to claim 1, wherein the temperature sensor measures only a temperature of the first plate.

3. The warm-cool beauty treatment device according to claim 1, further comprising:
   a timer to measure a time,
   wherein the controller controls a supply time of electric power to the Peltier element and the blower in correspondence with the measured time of the timer.

4. The warm-cool beauty treatment device according to claim 1,
   wherein the power supply includes a secondary battery to supply electric power to the Peltier element and/or the blower.

5. The warm-cool beauty treatment device according to claim 1, wherein the temperature sensor includes a thermistor.

6. The warm-cool beauty treatment device according to claim 1, wherein the first plate becomes warm and the second plate becomes cool by supplying electric power to the Peltier element from the power supply.

7. The warm-cool beauty treatment device according to claim 1, wherein the second surface has a penetrating hole into which the air flow is sent from the blower.

8. The warm-cool beauty treatment device according to claim 1, further comprising a casing accommodating the Peltier element, the heat sink, and the blower, and having a first opening exposing the first plate and a second opening exposing the second plate.

9. The warm-cool beauty treatment device according to claim 8,
   wherein the casing has at least one intake hole in accordance with the blower,
   wherein the second section of the heat sink has at least one through-hole in the direction of the stack and in accordance with the blower,
   wherein the casing has at least one exhaust hole in accordance with the through-hole.

10. The warm-cool beauty treatment device according to claim 1,
    wherein the first and second plates are for touching a human body.

11. The warm-cool beauty treatment device according to claim 1,
    wherein the second plate is disposed proximate the second surface of the Peltier element, a first surface of the first section of the heat sink is disposed proximate the first surface of the Peltier element and the first plate is disposed proximate a second surface of the first section of the heat sink, thereby forming a stack in a first direction,
    wherein the first section includes a first flat surface substantially perpendicular to the first direction of the stack, and the second section includes a blower connection surface substantially perpendicular to the first direction of the stack, and
    wherein the blower is in parallel with the Peltier element in a direction being different from the first direction of the stack.

12. The warm-cool beauty treatment device according to claim 11,
    wherein the second plate has at least one through-hole in a direction substantially parallel to the direction of the stack, and at least a part of the air flow generated by the blower passes through the at least one through-hole.

13. The warm-cool beauty treatment device according to claim 1,
    wherein the controller is programmed to control the supply of electric power to the Peltier element and the blower so that the electric power is supplied to the blower and is intermittently supplied to the Peltier element in response to the temperature measured by the temperature sensor being higher than the second temperature and lower than the third temperature.

14. The warm-cool beauty treatment device according to claim 13,
    wherein the controller is programmed to control the supply of electric power to the Peltier element and the blower so that the electric power is supplied to the Peltier element within an ON time and is not supplied to the Peltier element within an OFF time.

15. The warm-cool beauty treatment device according to claim 14,
    wherein the controller is programmed to set a first ON time as the ON time and a first OFF time as the OFF time in response to the temperature measured by the temperature sensor being higher than the second temperature and lower than a fourth temperature between the second and third temperatures, and
    wherein the controller is programmed to set a second ON time shorter than the first ON time as the ON time and a second OFF time longer than the first OFF time as the OFF time in response to the temperature measured by the temperature sensor being higher than the fourth temperature and lower than a fifth temperature between the fourth and third temperatures.

16. The warm-cool beauty treatment device according to claim 15,
    wherein the controller is programmed to set a third ON time shorter than the second ON time as the ON time and a third OFF time longer than the second OFF time as the OFF time in response to the temperature measured by the temperature being higher than the fifth temperature and lower than the third temperature.

* * * * *